United States Patent [19]

Buendia et al.

[11] 4,097,494

[45] Jun. 27, 1978

[54] NOVEL CYCLOPENTANONES

[75] Inventors: Jean Buendia, Nogent-sur-Marne; Jeanine Schalbar, Suresnes, both of France

[73] Assignee: Roussel Uclaf, Paris, France

[21] Appl. No.: 743,507

[22] Filed: Nov. 19, 1976

[30] Foreign Application Priority Data

Nov. 26, 1975 France .................................. 75 36161

[51] Int. Cl.² ...................... C07C 69/74; C07D 309/12
[52] U.S. Cl. ........................ 260/345.8 P; 260/345.9 P; 542/426; 560/122
[58] Field of Search ............. 260/468 K, 514 K, 345.8

[56] References Cited

U.S. PATENT DOCUMENTS

| 3,984,459 | 10/1976 | Babej et al. ............................. 260/468 |
| 4,014,919 | 3/1977 | Johnson et al. .......................... 260/468 |
| 4,039,563 | 8/1977 | Tanaka et al. ....................... 260/410.9 |

Primary Examiner—Robert Gerstl
Attorney, Agent, or Firm—Hammond & Littell

[57] ABSTRACT

Novel cyclopentanones of the formula

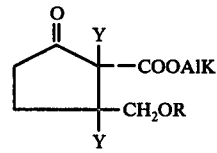

wherein AlK is alkyl of 1 to 4 carbon atoms, R is selected from the group of hydrogen and α-tetrahydropyranyl and the Ys are hydrogen or together represent a double bond with the proviso that when R is hydrogen, the Ys are hydrogen as well as products of the formula

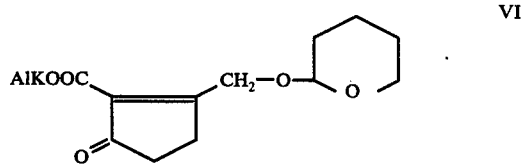

wherein AlK is alkyl of 1 to 4 carbon atoms and products of the formula

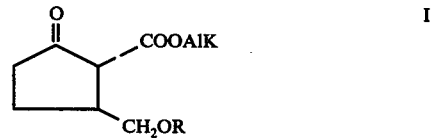

wherein R and AlK have the above definitions which are useful intermediates in the production of prostaglandins.

3 Claims, No Drawings

NOVEL CYCLOPENTANONES

OBJECTS OF THE INVENTION

It is an object of the invention to provide the novel intermediate products of formula Z, VI and I.

It is also an object of the invention to provide novel processes for the preparation of the said intermediate products.

These and other objects and advantages of the invention will become obvious from the following detailed description.

THE INVENTION

The novel intermediates of the invention have the formula

<chemical structure Z> wherein AlK is alkyl of 1 to 4 carbon atoms, R is selected from the group of hydrogen and α-tetrahydropyranyl and the Ys are hydrogen or together represent a double bond with the proviso that when R is hydrogen, the Ys are hydrogen as well as products of the formula <chemical structure VI> wherein AlK is alkyl of 1 to 4 carbon atoms and products of the formula

<chemical structure I> wherein R and AlK have the above definitions.

Examples of suitable alkyl radicals of 1 to 4 carbon atoms are methyl, ethyl, propyl, isopropyl, butyl, sec-butyl and tert.-butyl.

Among the preferred intermediates of the invention are methyl 2-(α-tetrahydropyranyloxymethyl)-5-oxo-1-cyclopentenecarboxylate, methyl 2-oxo-5-(α-tetrahydropyranyloxymethyl)-cyclopentanecarboxylate and methyl 2-oxo-5-hydroxymethyl-cyclopentanecarboxylate.

The novel process of the invention for the preparation of a compound of formula Z comprises reacting a compound of the formula <chemical structure II: CH₂—CH—CH₂OH with epoxide> with dihydropyran in the presence of an acid to obtain a compound of the formula <chemical structure III> reacting the latter with an alkyl acetylacetate with an alkyl of 1 to 4 carbon atoms in the presence of a strong base to form a compound of the formula <chemical structure IV> wherein AlK has the above definition and the wavy line indicates that the hydroxyl group is in one of the two possible positions with respect to the carbon atom, reacting the latter with an oxidation agent to form a compound of the formula <chemical structure V> reacting the latter with a base to form a compound of the formula

<chemical structure VI> reacting the latter with hydrogen in the presence of a catalyst to form a compound of the formula <chemical structure I'> which is a compound of formula Z wherein R is α-tetrahydropyranyl and Y is hydrogen and the said product may be treated with an acid to form a compound of the formula <chemical structure I''> which is the compound of formula Z wherein R and Y are hydrogen.

In a preferred embodiment of the said process, the acid used in the reaction of the compound of formula II with dihydropyran is p-toluene sulfonic acid although other acids such as oxalic acid or acetic acid may be used. The strong base used to treat the compound of formula III is preferably a mixture of sodium hydride and butyl lithium but equally useful is butyl lithium alone, potassium tertamylate or encombered amides such as lithium diisopropyl amides or a mixture of lithium diisopropyl amide and sodium hydride.

The oxidation reagent is preferably a complex of chromic acid and pyridine but also useful is chromic acid in triethylamine or a collidine. The base used to treat the compound of formula V is preferably potassium bicarbonate but other bases such as sodium bicarbonate or sodium or potassium carbonate may also be used. The hydrogenation catalyst is preferably palladized carbon but equally useful are palladized barium sulfate or strontium carbonate or Raney nickel. The acid used to treat a compound of formmula I' is preferably oxalic acid but equally useful are other acids such as acetic acid, hydrochloric acid or sulfuric acid.

Also as a part of the invention, the products of formula I may be prepared by treating a compound of formula VI with hydrogen in the presence of a catalyst to obtain a compound of formula I' which may be treated with an acid to form the compound of formula I''.

Other facets of the invention include the formation of a compound of formula VI by treating a compound of formula V with a strong base; the formation of a compound of formula V by reacting a compound of formula IV with an oxidizing agent; and the formation of a compound of formula IV by reacting a compound of formula II with dihydropyran in the presence of an acid to form a compound of formula III which is then reacted with an alkyl acetylacetate of 1 to 4 alkyl carbon atoms.

Among the novel intermediate products of the invention are compounds of the formula

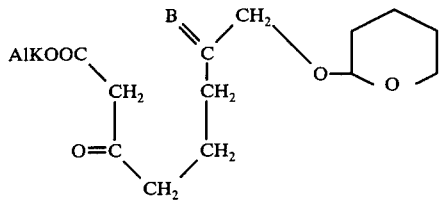

wherein AlK has the above definition and B is =O or

where the wavy line has the above meaning.

The compounds of formula IV may exist in the indicated form or in the following form

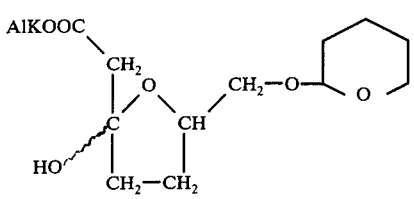
IVa

The compounds of formula Z and particularly those of formula I have a great industrial interest as they permit the realization of new synthesis of certain prostaglandin derivatives which new synthesis possess more advantages than known procedures to prepare the same compounds. In contrast to the processes of the prior art, the synthesis using a compound of formula Z as the intermediate is easier to use because they necessitate less purifications to obtain the intermediates and permit the obtention of better total yields.

The products of formula Z permit the preparation of prostaglandins having the 10,11-dihydro-$PGA_2$ skeleton and are useful for the preparation of compounds of the formula

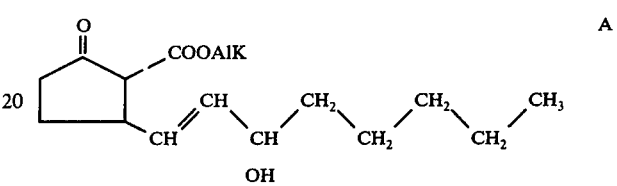
A wherein AlK has the above definition by reacting a compound of formula I'' with diazomethane to obtain a compound of the formula

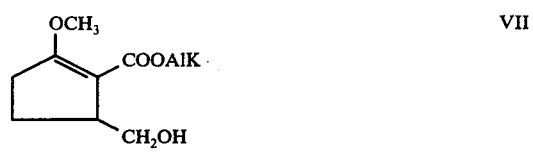
VII reacting the latter with an oxidation agent to obtain a compound of the formula

VIII treating the latter in the presence of a strong base with a phosphonate of the formula

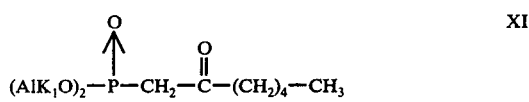
XI wherein $AlK_1$ is alkyl of 1 to 4 carbon atoms to obtain a compound of the formula

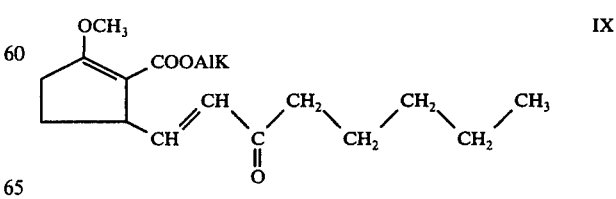
IX and reacting the latter with a reducing agent to form a compound of the formula

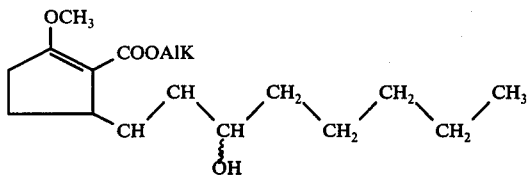

wherein AlK and the wavy line have the above definitions and treating the latter with an acid to form a compound of formula A.

In a preferred mode of the latter process, the oxidation agent used with the compound of formula VII is preferably a complex of chromic oxide and pyridine but also useful are chromic oxide and triethylamine or a collidine. The phosphonate reacted with a compound of formula VIII is preferably dimethyl (2-oxo-heptyl)-phosphonate but equally useful are the corresponding diethyl, dipropyl and dibutyl compounds. The strong base for this reaction is preferably sodium hydride although other bases such as sodium amide, sodium tert-amylate or butyl lithium may be used.

The reducing agent for treatment of the compound of formula IX is preferably sodium trismethoxy borohydride although other reducing agent such as sodium borohydride, potassium borohydride or zinc borohydride or alkyl borohydrides such as potassium or lithium tris-sec-butyl borohydrides may be used. The acid used to form the compound of formula A is preferably dilute hydrochloric acid but other mineral acids such as sulfuric acid may also be used.

French Pat. No. 2,085,652 describes the preparation of a compound of the formula

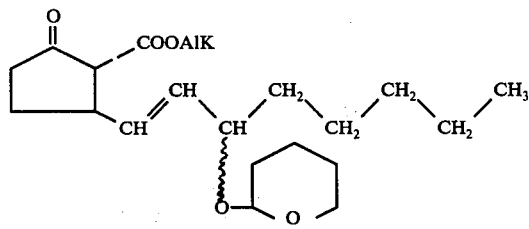

beginning from the compounds of formula A and French Pat. No. 2,085,654 describes using the compounds of formula E for the preparation of prostanoic acid derivatives with the skeleton of 10,11-dihydro-PGA$_2$ which possess interesting pharmacological properties.

The products of formula Z and particularly those of formula I are useful intermediates for the synthesis of cyclopentanol derivatives which have interesting pharmacological properties. In contrast to copending, commonly assigned U.S. Pat. application Ser. No. 717,048 filed Aug. 24, 1976 which describes a synthesis wherein a compound of formula A produced by the process of French Pat. No. 2,085,652 is reacted with diazomethane and the resulting product is oxidized with an oxidizing agent such as silver silicate, the synthesis using the compounds of formula Z is shorter. For example, the oxidation step is avoided and is easier to practice. Another object of the invention is a process for the preparation of a compound of formula IX beginning from a compound of formula I, comprising reacting a compound of formula I″ with diazomethane to obtain a compound of formula VII, oxidizing the latter with an oxidation agent to obtain the corresponding compound of formula VIII, reacting the latter with a phosphonate of formula XI in the presence of a strong base to form the corresponding compound of formula IX.

The synthesis of cyclopentanol derivatives starting from the compounds of formula IX is described in U.S. Pat. application Ser. No. 717,048 and comprises reacting a compound of formula IX with a compound of the formula

wherein Hal is halogen and R‴ is branched or straight chain, saturated or unsaturated aliphatic of 1 to 4 carbon atoms to obtain a compound of the formula

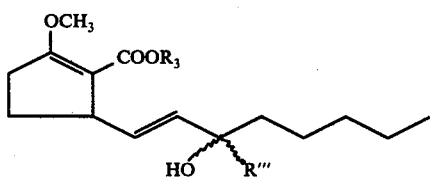

which is then treated with an acid such as hydrochloric acid to obtain a compound of the formula

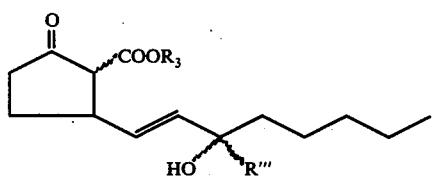

which may be either treated with a reducing agent such as sodium borohydride under mild conditions to form a compound of the formula

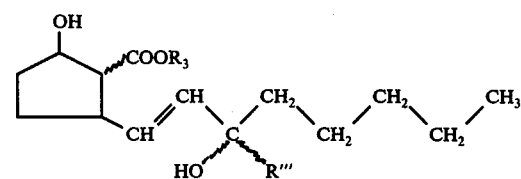

or reacted with 2,3-dihydropyran to obtain a compound of the formula

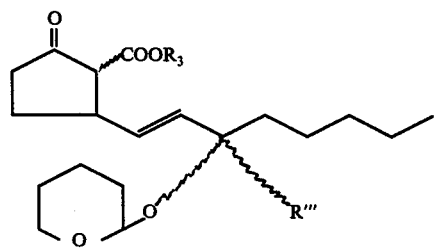

which may be treated with a reducing agent such as sodium borohydride under mild conditions to form a compound of the formula

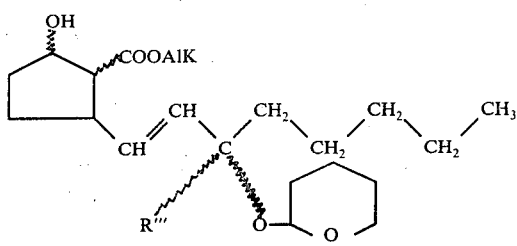

The compounds of formulae C and D are described in U.S. Pat. application Ser. No. 717,048 as having antagonistic properties against prostaglandin and having analgesic, anti-inflammatory and smooth muscle relaxant properties. They are useful for the treatment of pain affecting smooth muscles and articulations, pain, rhumatismal affections and affections due to a hyperactivity of certain smooth muscles.

In the following examples there are described several preferred embodiments to illustrate the invention. However, it is to be understood that the invention is not intended to be limited to the specific embodiments.

EXAMPLE 1 methyl (1RS, 5SR) 2-one-5-(α-tetrahydropyranyloxymethyl)-cyclopentanecarboxylate STEP A: 1,2-epoxy-3-α-tetrahydropyranyloxypropane A solution of 3.9 g of glycidol (2,3-epoxy-1-propanol), 18.5 ml of dihydropyran and 150 mg of p-toluene sulfonic acid was heated at 40° C for 30 minutes and another 150 mg of p-toluene sulfonic acid were added. After heating for 15 minutes, the mixture was cooled to room temperature and was neutralized with potassium carbonate. The mixture was filtered and was washed with ethyl acetate. The filtrate was evaporated to dryness under reduced pressure to obtain 8.48 g of 1,2-epoxy-3α-tetrahydropyranyloxypropane with an Rf = 0.6 (cyclohexane-ethyl acetate 8-2).

STEP B: methyl 3-keto-6-hydroxy-7α-tetrahydropyranyloxyheptanoate

A solution of 8 ml of methyl acetate and 16 ml of anhydrous tetrahydrofuran was added over 30 minutes at 0° C to a suspension of 3.554 g of sodium hydride in 50% oil in 16 ml of anhydrous tetrahydrofuran and then 39 ml of butyl lithium were added thereto over 30 minutes. The mixture was stirred at −70° C for 30 minutes and the solution was added over 45 minutes at 0° C to a solution of 5.8 g of 1,2-epoxy-3α-tetrahydropyranyloxypropane in 16 ml of tetrahydrofuran. The mixture was stirred for 3½ hours and was then poured into an excess of a concentrated solution of iced monosodium phosphate. The mixture was stirred for 10 minutes and was then extracted with ethyl acetate. The extracts were washed until the wash water was neutral. The extracts were evaporated to dryness to obtain 16.9g of oil which was chromatographed over silica gel. Elution with a 6-4 cyclohexane-ethyl acetate mixture to obtain 8.02g of methyl 3-keto-6-hydroxy-7α-tetrahydropyranyloxyheptanoate with an Rf = 0.15.

STEP C: methyl 3,6-dioxo-7α-tetrahydropyranyloxyheptanoate 6 g of chromic acid were slowly added to a solution of 9.7 ml of pyridine in 148 ml of methylene chloride and after stirring for 15 minutes, a solution of 1.1 g of the product of Step B in 10 ml of methylene chloride was added. After 15 minutes, 150 ml of ether were added and the mixture was filtered. The recovered precipitate was washed with ether and the filtrate was evaporated to dryness to obtain 1.3 g of raw product. The latter was chromatographed over silica gel and was eluted with an 8-2 methylene chloride-ethyl acetate mixture to obtain 473 mg of methyl 3,6-dioxo-7α-tetrahydropyranyloxyheptanoate with an Rf = 0.45.

STEP D: methyl 2-(α-tetrahydropyranyloxymethyl)-5-oxo-1-cyclopentenecarboxylate

A solution of 220 mg of the raw product of Step C in 2.4 ml of methylene chloride was added to a vigorously stirred solution of 291 mg of sodium bicarbonate in 72 ml of distilled water and after 30 minutes, the mixture was adjusted to a pH of 3 with oxalic acid. The mixture was saturated with sodium chloride and was extracted with methylene chloride. The extracts were evaporated to dryness to obtain 205 mg of methyl 2-(α-tetrahydropyranyloxymethyl)-5-oxo-1-cyclopentenecarboxylate.

STEP E: methyl (1RS, 5SR) 2-oxo-5-(α-tetrahydropyranyloxymethyl)-cyclopentanecarboxylate A solution of 215mg of the product of Step D, 10 ml of methanol and 21 mg of 10% palladized carbon was stirred under a hydrogen atmosphere for 40 minutes during which the theoretical amount of hydrogen was absorbed and the mixture was filtered. The filter was washed with ethyl acetate and the filtrate was evaporated to dryness to obtain 172 mg of an oil. The latter was chromatographed over silica and was eluted with a 50—50 cyclohexane-ethyl acetate mixture to obtain 122 mg of methyl (1RS, 5SR) 2-oxo-5-(α-tetrahydropyranyloxymethyl)-cyclopentanecarboxylate.

EXAMPLE 2 methyl (1RS, 5SR) 2-oxo-5-hydroxymethyl-cyclopentanecarboxylate

A mixture of 43 g of the product of Example 1, 860 ml of methanol, 86 ml of water and 12.7 g of oxalic acid was stirred at 60° C for 3 hours and was concentrated under reduced pressure at 40° C. The residue was taken up in chloroform and the solution was washed with water and dried and evaporated to dryness to obtain 29.2 g of raw product. The latter was chromatographed over silica gel and was eluted with a 2-8 cyclohexane-ethyl acetate mixture to obtain 14 g of methyl (1RS, 5SR)-2-oxo-5-hydroxymethyl-cyclopentanecarboxylate in the form of an oil with an RMN spectrum in CDCl₃ of 90 MHz.

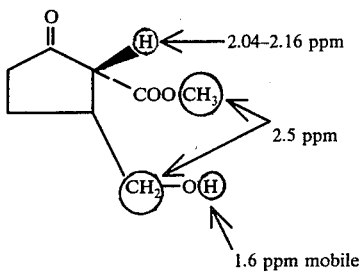

EXAMPLE 3 methyl (5RS, 1'E) 2-methoxy-5-(3'-oxo-1'-octenyl)-1-cyclopentenecarboxylate

STEP A: methyl (5RS) 2-methoxy-5-hydroxymethyl-1-cyclopentenecarboxylate

A mixture of 4 g of the β-keto ester of Example 2, 10 ml of methylene chloride and 50 ml of diazomethane in methylene chloride was stirred for 4 hours at room temperature and the diazomethane and solvent were evaporated to obtain 4.3 g of a raw yellow oil which was used as is for the next step.

STEP B: methyl (5RS) 2-methoxy-5-formyl-1-cyclopentenecarboxylate 25.5 g of chromic oxide were added in small fractions at 15° to 20° C to a solution of 41 ml of pyridine in 400ml of anhydrous methylene chloride and the mixture was stirred for 15 minutes. The mixture was cooled to −15° C and a solution of 4.3 g of the product of Step A in 10 ml of methylene chloride was added thereto. After 1½ hours, 50 g of celite and 100 ml of ether were added thereto and the mixture was filtered. The filtrate was washed with ether and the filtrate was evaporated to dryness at 30° C to obtain methyl (5RS) 2-methoxy-5-formyl-1-cyclopentenecarboxylate.

STEP C: methyl (5RS, 1'E) 2-methoxy-5-(3'-oxo-1'-octenyl)-1-cyclopentenecarboxylate A solution of 50 ml of dimethoxyethane and 7.743 g of dimethyl (2-oxoheptyl)-phosphonate was added dropwise to a suspension of 1.672 g of sodium hydride in 50% oil in 50 ml of dimethoxyethane and the mixture was stirred for 3 hours. A solution of the product of Step B in 50 ml of dimethoxyethane was added thereto over 20 minutes and after 2 hours, the mixture was poured into an iced solution of monosodium phosphate. The mixture was extracted with ethyl acetate and the extracts were washed with water, dried and evaporated to dryness to obtain 12 g of an oil. The latter was chromatographed over silica gel and was eluted with a 60-40 cyclohexane-ethyl acetate mixture to obtain 2.142 g of methyl (5RS, 1'E) 2-methoxy-5-(3'-oxo-1'-octenyl)-1-cyclopentenecarboxylate as a colorless oil.

I.R. Spectrum:

C=O weak and large max. at 1691 cm$^{-1}$, C=C conjugation at 1623 cm$^{-1}$.

EXAMPLE 4 methyl (1RS, 5RS, 1'E, 3'RS & SR) -2-oxo-5-(3'-hydroxy-1'-octenyl)-cyclopentanecarboxylate

STEP A: methyl (5RS, 1'E, 3'RS & SR) 2-methoxy-5-(3'-hydroxy-1'-octenyl)-1-cyclopentenecarboxylate 55 mg of sodium trismethoxyborohydride were added to 76.7 mg of the product of Example 3 in 3 ml of tetrahydrofuran under a nitrogen atmosphere and after 30 minutes, a few drops of acetone were added. The mixture was hydrolyzed with iced monosodium phosphate and the mixture was extracted with ethyl acetate. The extracts were washed with aqueous sodium chloride solution, were dried and evaporated to dryness under reduced pressure to obtain methyl (5RS, 1'E, 3'RS & SR) 2-methoxy-5-(3'-hydroxy-1'-octenyl)-1-cyclopentenecarboxylate.

STEP B: methyl (1RS, 5RS, 1'E, 3'RS & SR) 2-oxo-5-(3'-hydroxy-1'-octenyl)-cyclopentanecarboxylate The residue of Step A was added under reduced nitrogen to 4 ml of methanol, 0.4 ml of water and a few drops of N hydrochloric acid and after stirring for 3 hours, the methanol was evaporated under reduced pressure. The residue was taken up in a monosodium phosphate solution and was extracted with ethyl acetate. The extracts were washed with water, dried and evaporated to dryness. The residue was chromatographed over silica gel and was eluted with a 60-40 cyclohexane-ethyl acetate mixture to obtain 35.1 mg of a mixture of methyl (1RS, 5RS, 1'E, 3'RS & SR) 2-oxo-5-(3'-hydroxy-1'-octenyl)-cyclopentanecarboxylate.

I.R. Spectrum:

OH at 3600 cm$^{-1}$, C=O at 1737 and 1728 cm$^{-1}$ and —CH=CH— at 975 cm$^{-1}$.

The two isomers were separated by chromatography over a plate and elution with a 60-40 benzene-ethyl acetate mixture containing 0.1% triethylamine to obtain the 3'RS isomer (after 2 migrations) with an Rf = 0.51 and the 3'SR isomer with an RF = 0.44.

EXAMPLE 5 methyl (1RS, 2SR, 5RS, 3'SR) (1'E) 2-hydroxy-5-(3'-hydroxy-3'-ethynyl-1'-octenyl)-cyclopentanecarboxylate

STEP A: methyl (5RS, 3'RS, 1'E) 2-methoxy-5-(3'-hydroxy-3'-ethynyl-1'-octenyl)-1-cyclopentenecarboxylate and methyl (5RS, 3'SR, 1'E) 2-methoxy-5-(3'-hydroxy-3'-ethynyl-1'-octenyl)-1-cyclopentenecarboxylate 3.3 ml of a solution of 0.9 M of ethynyl magnesium bromide [prepared from ethyl magnesium bromide and acetylene in tetrahydrofuran] were added at −10° C to a solution of 635 mg of methyl (5RS, 1'E) 2-methoxy-5-(3'-oxo-1'-octenyl)-1-cyclopentenecarboxylate in 10 ml of tetrahydrofuran and the mixture was stirred at −5° C until the starting material disappeared. Then, the mixture was poured into a saturated ammonium chloride solution and the mixture was extracted with ether. The ether extracts were dried and evaporated to dryness. The residue was chromatographed over silica gel and was eluted with a 9-1 methylene chloride-ethyl acetate mixture containing 0.5% of triethylamine to obtain the above indicated α-OH and β-OH isomers.

STEP B: methyl (1RS, 5RS, 3'SR, 1'E) 2-oxo-5-(3'hydroxy-3'-ethynyl-1'-octenyl)-cyclopentanecarboxylate A mixture of 1.1 g of the α-OH isomer of Step A, 35 ml of ethanol, 3.5 ml of water and 0.87 ml of 1N hydrochloric acid was stirred at 20° C for 70 hours and was poured into water. The mixture was extracted with ethyl acetate and ethyl acetate extracts were washed with water, dried and evaporated to dryness. The residue was chromatographed over silica gel and was eluted with an 8-2 benzene-ethyl acetate mixture to obtain methyl (1RS, 5RS, 3'SR, 1'E) 2-oxo-5-(3'- hydroxy-3'-ethynyl-1'-octenyl)-cyclopentanecarboxylate

STEP C: methyl (1RS, 2SR, 5RS, 3'SR, 1'E) 2-hydroxy-5-(3'-hydroxy-3'-ethynyl-1'-octenyl)-cyclopentanecarboxylate 53 mg of sodium borohydride were added at 5° C to a mixture of 375 mg of the product of Step B, 10 ml of ethanol and 1 ml of water and the mixture was stirred for 2 hours. The mixture was taken up in water and the mixture was extracted with methylene chloride. The organic extracts were washed with water, dried and evaporated to dryness. The residue was chromatographed over silica gel and was eluted with an 8-2 benzene-ethyl acetate mixture to obtain methyl (1RS, 2SR, 5RS, 3'SR, 1'E) 2-hydroxy-5-(3'-hydroxy-3'-ethynyl-1'-octenyl)-cyclopentanecarboxylate.

Various modifications of the products and process of the invention may be made without departing from the spirit or scope thereof and it should be understood that the invention is to be limited only as defined in the appended claims.

We claim:

1. A compound of the formula

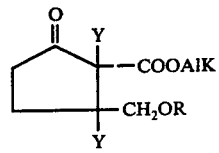

wherein AlK is alkyl of 1 to 4 carbon atoms, R is selected from the group consisting of hydrogen and α-tetrahydropyranyl and Ys are hydrogen.

2. A compound of claim 1 which is methyl 2-oxo-5-(α-tetrahydropyranyloxymethyl)-cyclopentanecarboxylate.

3. A compound of claim 1 which is methyl 2-oxo-5-hydroxymethyl-cyclopentanecarboxylate.

* * * * *